US012685297B2

(12) United States Patent
Hsu et al.

(10) Patent No.: US 12,685,297 B2
(45) Date of Patent: Jul. 21, 2026

(54) GENETICALLY MODIFIED MOUSE, METHODS FOR PRODUCING THE SAME, AND USES THEREOF

(71) Applicant: MacKay Memorial Hospital, Taipei City (TW)

(72) Inventors: Kate Hsu, New Taipei City (TW); Li-Yang Chen, New Taipei City (TW); Pin-Lung Chen, New Taipei City (TW)

(73) Assignee: MacKay Memorial Hospital, Taipei City (TW)

( * ) Notice: Subject to any disclaimer, the term of this patent is extended or adjusted under 35 U.S.C. 154(b) by 385 days.

(21) Appl. No.: 18/397,846

(22) Filed: Dec. 27, 2023

(65) Prior Publication Data

US 2025/0212856 A1 Jul. 3, 2025

(51) Int. Cl.
*A01K 67/0278* (2024.01)
*C12N 9/22* (2006.01)

(52) U.S. Cl.
CPC ............ *A01K 67/0278* (2013.01); *C12N 9/22* (2013.01); *A01K 2217/07* (2013.01); *A01K 2227/105* (2013.01); *A01K 2267/0375* (2013.01); *C12N 2310/20* (2017.05)

(58) Field of Classification Search
CPC ............ A01K 67/0275; A01K 67/0278; A01K 2207/15; A01K 2207/072
See application file for complete search history.

(56) References Cited

U.S. PATENT DOCUMENTS

2002/0012660 A1* 1/2002 Colman ............... C12N 15/907
800/14

FOREIGN PATENT DOCUMENTS

WO WO-2016144642 A1 * 9/2016 ........... C12N 5/0641

OTHER PUBLICATIONS

Auffray et al. GlycophorinA dimerization and band 3 interaction during erythroid membrane biogenesis: in vivo studies in human glycophorinA transgenic mice. Blood 2001, 97;9:2872-2878. (Year: 2001).*

Hsu et al. Miltenberger blood group antigen type III (Mi.III) enhances the expression of band 3. Blood 2009, 114;9:1919-1928. (Year: 2009).*

NCBI webpage capture. GenBank: EU338225.1, submitted 2009. https://www.ncbi.nlm.nih.gov/nuccore/EU338225.1. Retrieved Dec. 3, 2026. (Year: 2009).*

Chen et al. Influence of hemoglobin on blood pressure among people with GP.Mur blood type. Journal of the Formosan Medical Association 2022, 121:1721-1727. (Year: 2022).*

Vrankova et al. Comparison of the effects of indapamide and captopril on the development of spontaneous hypertension. Journal of Hypertension 2009, 27(S6):S42-S46. (Year: 2009).*

* cited by examiner

*Primary Examiner* — Christopher M Babic
*Assistant Examiner* — Jennifer S Spence
(74) *Attorney, Agent, or Firm* — NZ Carr Law Office

(57) ABSTRACT

Disclosed herein is a genetically modified mouse whose genome comprises a transgene encoding a Miltenberger blood group antigen subtype III (Mi.II antigen). According to embodiments of the present disclosure, the Mi.III antigen comprises the amino acid sequence of SEQ ID NO: 1. Also disclosed herein are a method of producing the genetically modified mouse, and uses of the genetically modified mouse in selecting a drug candidate for treating hypertension.

17 Claims, 1 Drawing Sheet

Specification includes a Sequence Listing.

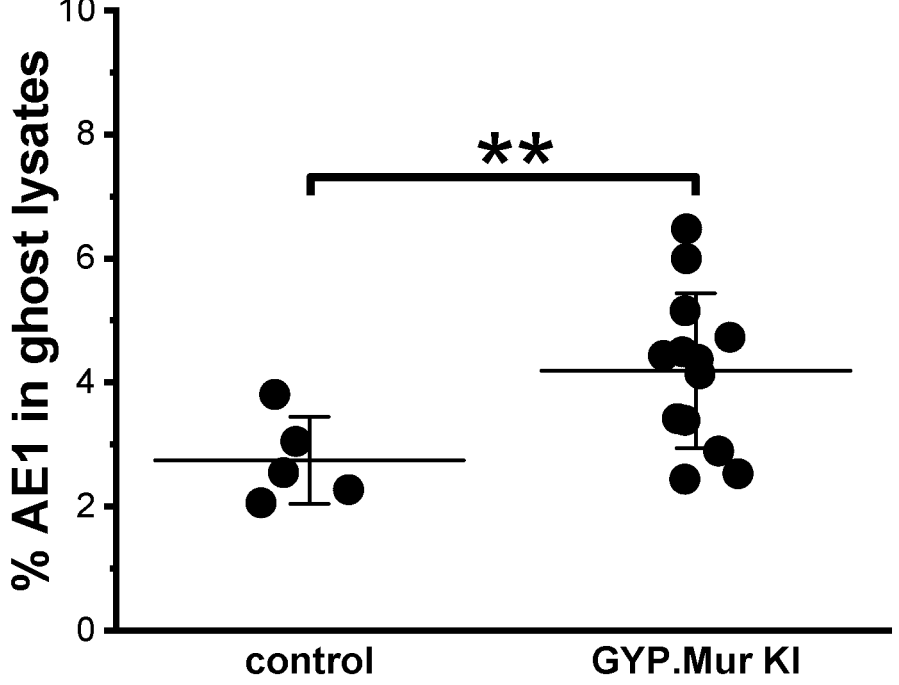

SEQUENCE LISTING

```
Sequence total quantity: 18
SEQ ID NO: 1            moltype = AA   length = 122
FEATURE                 Location/Qualifiers
source                  1..122
                        mol_type = protein
                        organism = synthetic construct
SEQUENCE: 1
MYGKIIFVLL LSEIVSISAL STTEVAMHTS TSSSVTKSYI SSQTNDKHKR DTYPAHTANE   60
VSEISVRTVY PPEEETGETG QLVHRFTVPA PVVIILIILC VMAGIIGTIL LISYSIRRLI  120
KA                                                                 122

SEQ ID NO: 2            moltype = DNA   length = 369
FEATURE                 Location/Qualifiers
source                  1..369
                        mol_type = other DNA
                        organism = synthetic construct
SEQUENCE: 2
atgtatggaa aaataatctt tgtattacta ttgtcagaaa ttgtgagcat atcagcatta   60
agtaccactg aggtggcaat gcacacttca acctcttctt cagtcacaaa gagttacatc  120
tcatcacaga caaatgataa gcacaaacgg gacacatatc cagctcatac tgctaatgaa  180
gtttcagaaa tttctgttag aactgtttac cctccagaag aggaaaccgg agaaacggga  240
caacttgtcc atcgtttcac tgtaccagct cctgtagtga taatactcat tattttgtgt  300
gtgatggctg gtattattgg aacgatcctc ttaatttctt acagtattcg ccgactgata  360
aaggcatga                                                          369

SEQ ID NO: 3            moltype = DNA   length = 968
FEATURE                 Location/Qualifiers
source                  1..968
                        mol_type = other DNA
                        organism = synthetic construct
SEQUENCE: 3
acaaaaccaa gttcaataga agggggtaca aaccagtacc accacgaaca agcacttctg   60
tttccccggt gatgtcgtat agactgcttg cgtggttgaa agcgacggat ccgttatccg  120
cttatgtact tcgagaagcc cagtaccacc tcggaatctt cgatgcgttg cgctcagcac  180
tcaaccccag agtgtagctt aggctgatga gtctggacat ccctcaccgg tgacggtggt  240
```

-continued

```
ccaggctgcg ttggcggcct acctatggct aacgccatgg gacgctagtt gtgaacaagg    300
tgtgaagagc ctattgagct acataagaat cctccggccc ctgaatgcgg ctaatcccaa    360
cctcggagca ggtggtcaca aaccagtgat tggcctgtcg taacgcgcaa gtccgtggcg    420
gaaccgacta ctttgggtgt ccgtgtttcc ttttatttta ttgtggctgc ttatggtgac    480
aatcacagat tgttatcata aagcgaattg gataggatca agcttatcga taccgtcgac    540
ctcgagctca agcttcgaat tctttgcact aacttcagga accagctcat gatctcagga    600
tgtatggaaa aataatcttt gtattactat tgtcagaaat tgtgagcata tcagcattaa    660
gtaccactga ggtggcaatg cacacttcaa cctcttcttc agtcacaaag agttacatct    720
catcacagac aaatgataag cacaaacggg acacatatcc agctcatact gctaatgaag    780
tttcagaaat ttctgttaga actgtttacc ctccagaaga ggaaaccgga gaaacgggac    840
aacttgtcca tcgtttcact gtaccagctc ctgtagtgat aatactcatt attttgtgtg    900
tgatggctgg tattattgga acgatcctct taatttctta cagtattcgc cgactgataa    960
aggcatga                                                             968

SEQ ID NO: 4                moltype = DNA  length = 20
FEATURE                     Location/Qualifiers
source                      1..20
                            mol_type = other DNA
                            organism = synthetic construct
SEQUENCE: 4
tgaggtcttt caaacattgg                                                20

SEQ ID NO: 5                moltype = DNA  length = 100
FEATURE                     Location/Qualifiers
misc_feature                1..20
                            note = DNA
source                      1..100
                            mol_type = other DNA
                            organism = synthetic construct
misc_feature                21..100
                            note = RNA
SEQUENCE: 5
tgaggtcttt caaacattgg gttttagagc tagaaatagc aagttaaaat aaggctagtc    60
cgttatcaac ttgaaaaagt ggcaccgagt cggtgctttt                          100

SEQ ID NO: 6                moltype = DNA  length = 2138
FEATURE                     Location/Qualifiers
source                      1..2138
                            mol_type = other DNA
                            organism = synthetic construct
SEQUENCE: 6
ggttcactgg ggatgtctgg gagaccgtct tgtggcacca aactcagctt ctcagcaggc    60
acaagaaacc attattccta agagtggcat cacagacttg acagcctacc ttcaatttga    120
atacatgtat ctaaatcaac ttacttcatt actgccttag cactaggctc tgcctctacc    180
ttcctatgag tttctcatct ctagagaaag gagcaggaga agtgtgcttg tttctcaccc    240
aagatttcta gaataaattt tctaaaggaa aaaaatctgt gcctttctaa aacaaacaaa    300
tggaaatcct caagtagaga taaatgaaag atattttaca attatattca gtctactcca    360
agagtgtaga atccaggtat atatttggtg caatgatttc gtgttatttt aagtataact    420
gtgtcttatg tgactgcttt gtaacccccc tcaatcccat ccttctacag actcctaatg    480
aagagtcctc caacgtctaa tgtacaagtg tggcggctag tactccggta ttgcggtacc    540
cttgtacgcc tgttttatac tcccttcccg taacttagac gcacaaaacc aagttcaata    600
gaaggggggta caaaccagta ccaccacgaa caagcacttc tgtttccccg gtgatgtcgt    660
atagactgct tgcgtggttg aaagcgacgg atccgttatc cgcttatgta cttcgagaag    720
cccagtacca cctcggaatc ttcgatgcgt tgcgctcagc actcaacccc agagtgtagc    780
ttaggctgat gagtctggac atccctcacc ggtgacggtg gtccaggctg cgttggcggc    840
ctacctatgg ctaacgccat gggacgctag ttgtgaacaa ggtgtgaaga gcctattgag    900
ctacataaga atcctccggc ccctgaatgc ggctaatccc aacctcggag caggtggtca    960
caaaccagtg attggcctgt cgtaacgcgc aagtccgtgg cggaaccgac tactttgggt    1020
gtccgtgttt cctttttttt tattgtggct gcttatggtg acaatcacag attgttatca    1080
taaagcgaat tggataggat caagcttatc gataccgtcg acctcgagct caagcttcga    1140
attctttgca ctaacttcag gaaccagctc atgatctcag gatgtatgga aaaataatct    1200
ttgtattact attgtcagaa attgtgagca tatcagcatt aagtaccact gaggtggcaa    1260
tgcacacttc aacctcttct tcagtcacaa agagttacat ctcatcacag acaaatgata    1320
agcacaaacg ggacacatat ccagctcata ctgctaatga atttcagaaa atttctgtta    1380
gaactgttta ccctccagaa gaggaaaccg gagaaacggg acaacttgtc catcgtttca    1440
ctgtaccagc tcctgtagtg ataatactca ttattttgtg tgtgatggct ggtattattg    1500
gaacgatcct cttaatttct tacagtattc gccgactgat aaaaggcatg atcttgcctag    1560
aaccggctgc acctgctgtt ctcttgttta tgcaaactgg ctgcacctgc tattcctttg    1620
cttatgccga attctgcaga tgtttgaaag acctcaagga aaacaagact tcaatcaatg    1680
ggaaaaataa tcggctgtgt cagtaaaatta tgtaccttcc tgagctacac cattgtaaga    1740
agaaaatgcc acctttggag tctgtgattc actatgggga tggggaaact ctgttaatta    1800
ataactgatg atgaacaaga gcttccttgt atgcttgatt ttgctcgcag aaattttttgt    1860
aactgcttga ctagatattt tactcaaaaa tttcaattga gtttgtgtgc cgtcctttaa    1920
ggctgatgta ttcaactctg ttatggtttg ttcctggtga catcacagaa gggctttttac    1980
tgtctccatg aaatccaaga ttcctcatcg cttcaacccc agagcccatt tttatttaat    2040
ttaagtaaat taaaagacca gtaagtcttc ccgtgttctt ccttgccagg caggcagcac    2100
acagctctct tactgggaag gatgctttgc caacactc                           2138

SEQ ID NO: 7                moltype = DNA  length = 493
```

-continued

```
FEATURE               Location/Qualifiers
source                1..493
                      mol_type = other DNA
                      organism = synthetic construct
SEQUENCE: 7
ggttcactgg ggatgtctgg gagaccgtct tgtggcacca aactcagctt ctcagcaggc    60
acaagaaacc attattccta agagtggcat cacagacttg acagcctacc ttcaatttga   120
atacatgtat ctaaatcaac ttacttcatt actgccttag cactaggctc tgcctctacc   180
ttcctatgag tttctcatct ctagagaaag gagcaggaga agtgtgcttg tttctcaccc   240
aagatttcta gaataaattt tctaaaggaa aaaaatctgt gcctttctaa aacaaacaaa   300
tggaaatcct caagtagaga taaatgaaag atatttaca attatattca gtctactcca    360
agagtgtaga atccaggtat atatttggtg caatgatttc gtgttatttt aagtataact   420
gtgtcttatg tgactgcttt gtaacccccc tcaatcccat ccttctacag actcctaatg   480
aagagtcctc caa                                                      493

SEQ ID NO: 8         moltype = DNA  length = 499
FEATURE              Location/Qualifiers
source               1..499
                     mol_type = other DNA
                     organism = synthetic construct
SEQUENCE: 8
atgtttgaaa gacctcaagg aaaacaagac ttcaatcaat gggaaaaata atcggctgtg    60
tcagtaaatt atgtaccttc ctgagctaca ccattgtaag aagaaatgc caccttttgga   120
gtctgtgatt cactatgggg atggggaaac tctgttaatt aataactgat gatgaacaag   180
agcttccttg tatgcttgat tttgctcgca gaaattttg taactgcttg actagatatt    240
ttactcaaaa atttcaattg agtttgtgtg ccgtccttta aggctgatgt attcaactct    300
gttatggttt gttcctggtg acatcacaga agggctttta ctgtctccat gaaatccaag    360
attcctcatc gcttcaaccc cagagcccat ttttatttaa tttaagtaaa ttaaaagacc    420
agtaagtctt cccgtgttct tccttgccag gcaggcagca cacagctctc ttactgggaa    480
ggatgctttg ccaacactc                                                499

SEQ ID NO: 9         moltype = RNA  length = 80
FEATURE              Location/Qualifiers
source               1..80
                     mol_type = other RNA
                     organism = synthetic construct
SEQUENCE: 9
gttttagagc tagaaatagc aagttaaaat aaggctagtc cgttatcaac ttgaaaaagt    60
ggcaccgagt cggtgctttt                                                80

SEQ ID NO: 10        moltype = DNA  length = 20
FEATURE              Location/Qualifiers
source               1..20
                     mol_type = other DNA
                     organism = synthetic construct
SEQUENCE: 10
ggcatcaatc ggcaagaatg                                                20

SEQ ID NO: 11        moltype = DNA  length = 20
FEATURE              Location/Qualifiers
source               1..20
                     mol_type = other DNA
                     organism = synthetic construct
SEQUENCE: 11
gtcgctttca accacgcaag                                                20

SEQ ID NO: 12        moltype = DNA  length = 24
FEATURE              Location/Qualifiers
source               1..24
                     mol_type = other DNA
                     organism = synthetic construct
SEQUENCE: 12
gtgatggctg gtattattgg aacg                                           24

SEQ ID NO: 13        moltype = DNA  length = 24
FEATURE              Location/Qualifiers
source               1..24
                     mol_type = other DNA
                     organism = synthetic construct
SEQUENCE: 13
aatgagggct gtgagtgtcc ttac                                           24

SEQ ID NO: 14        moltype = DNA  length = 18
FEATURE              Location/Qualifiers
source               1..18
                     mol_type = other DNA
                     organism = synthetic construct
SEQUENCE: 14
cagacaaatg ataagcac                                                  18
```

-continued

```
SEQ ID NO: 15              moltype = DNA  length = 23
FEATURE                    Location/Qualifiers
source                     1..23
                           mol_type = other DNA
                           organism = synthetic construct
SEQUENCE: 15
ggcataagca aaggaatagc agg                                            23

SEQ ID NO: 16              moltype = DNA  length = 19
FEATURE                    Location/Qualifiers
source                     1..19
                           mol_type = other DNA
                           organism = synthetic construct
SEQUENCE: 16
gttgtctcct gcgacttca                                                 19

SEQ ID NO: 17              moltype = DNA  length = 19
FEATURE                    Location/Qualifiers
source                     1..19
                           mol_type = other DNA
                           organism = synthetic construct
SEQUENCE: 17
ggaagatggt gatgggatt                                                 19

SEQ ID NO: 18              moltype = AA  length = 22
FEATURE                    Location/Qualifiers
source                     1..22
                           mol_type = protein
                           organism = synthetic construct
SEQUENCE: 18
QDYPLQQTYA PVVMKPKPQG PV                                             22
```

GENETICALLY MODIFIED MOUSE, METHODS FOR PRODUCING THE SAME, AND USES THEREOF

SEQUENCE LISTING XML

The present application is being filed along with a Sequence Listing XML in electronic format. The Sequence Listing XML is provided as an XML file entitled P4362_SEQ_AF, created Dec. 15, 2023, which is 22 Kb in size. The information in the electronic format of the Sequence Listing XML is incorporated herein by reference in its entirety.

BACKGROUND OF THE INVENTION

1. Field of the Invention

The present disclosure in general relates to the field of genetically modified animals. More particularly, the present disclosure relates to genetically modified mice expressing human Miltenberger blood group antigen subtype III (Mi.III antigen), and their uses in selecting drug candidates for treating hypertension

2. Description of Related Art

Hypertension (also known as "high blood pressure" or "raised blood pressure") is a medical condition in which the blood vessels have persistently raised pressure. Blood pressure is measured in units of millimeters of mercury (mmHg). In general, the systolic blood pressure and diastolic blood pressure at rest are respectively 100-130 mmHg and 60-80 mmHg. Hypertension is defined as a systolic blood pressure higher than 130 mmHg or a diastolic blood pressure higher than 80 mmHg. However, it is a major risk factor for stroke, coronary artery disease, heart failure, atrial fibrillation, peripheral arterial disease, vision loss, chronic kidney disease, and dementia. Further, hypertension is a major cause of premature death worldwide.

Currently, the drug research and development is mainly based on in vitro systems. Nonetheless, hypertension is a multi-factorial disease involving genetic and various environmental factors, and the in vitro systems cannot adequately reflect in vivo conditions, resulting in a high failure rate in drug development. In view of the forgoing, there exists a need of a hypertension animal model for the selection or identification of anti-hypertension drugs in a more accurate and efficient manner.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a genetically modified mouse whose genome comprises a transgene encoding a Miltenberger blood group antigen subtype III (Mi.III antigen; also known as "GP.Mur antigen" or "GP.Mur", an antigen encoded by "GYP.Mur" gene). According to embodiments of the present disclosure, the Mi.III antigen comprises the amino acid sequence of SEQ ID NO: 1.

According to some embodiments of the present disclosure, the transgene is a complementary deoxyribonucleic acid (cDNA) of GYP.Mur gene and comprises a nucleotide sequence at least 85% identical to SEQ ID NO: 2. Preferably, the transgene comprises a nucleotide sequence 100% identical to SEQ ID NO: 2, i.e., comprising the nucleotide sequence of SEQ ID NO: 2.

According to some embodiments of the present disclosure, the transgene comprises an internal ribosome entry site (IRES), and a cDNA of GYP.Mur gene linked to the 3' end of the IRES. In these embodiments, the transgene comprises a nucleotide sequence at least 85% identical to SEQ ID NO: 3. In one example, the transgene comprises a nucleotide sequence 100% identical to SEQ ID NO: 3, i.e., comprising the nucleotide sequence of SEQ ID NO: 3.

According to certain embodiments of the present disclosure, the transgene is inserted at the 3' untranslated region (UTR) of endogenous glycophorin A (GYPA) gene of the genetically modified mouse.

Another aspect of the present disclosure pertains to a method of producing the present genetically modified mouse. The method comprises, (a) introducing the transgene into endogenous GYPA gene of a zygote or embryo of a mouse; and (b) transplanting the zygote or embryo of step (a) into a recipient mouse to produce the genetically modified mouse.

According to certain embodiments of the present disclosure, in step (a), the transgene is introduced into the endogenous GYPA gene by the steps of, (a-1) providing a single guide ribonucleic acid (sgRNA) comprising the nucleotide sequence of SEQ ID NO: 4;

(a-2) providing a donor template comprising the transgene, a 5' homologous arm, and a 3' homologous arm, wherein the 5' and 3' homologous arms are respectively linked to the 5' end and 3' end of the transgene, and respectively comprise the nucleotide sequences of SEQ ID NOs: 7 and 8; and (a-3) injecting the sgRNA of (a-1), the donor template of (a-2) and a CRISPR associated protein 9 (Cas9) into the zygote or embryo.

As described above, the transgene may comprise the nucleotide sequence of SEQ ID NO: 2 (GYP.Mur cDNA) or SEQ ID NO: 3 (IRES+GYP.Mur cDNA). According to certain preferred embodiments, the transgene comprises the nucleotide sequence of SEQ ID NO: 3. In these embodiments, the donor template comprises the nucleotide sequence of SEQ ID NO: 6.

According to some exemplary embodiments, the sgRNA comprises a crRNA (SEQ ID NO: 4) and a scaffold fragment (SEQ ID NO: 9) linked to the crRNA. In this case, the sgRNA comprises the nucleotide sequence of SEQ ID NO: 5.

Also disclosed herein is a method of identifying a drug for treating hypertension in a subject by using the genetically modified mouse of the present disclosure. The method comprises, (a) administering a drug candidate to the genetically modified mouse;

(b) measuring the blood pressure of the genetically modified mouse of step (a); and (b) identifying the drug candidate to be the drug when the measured blood pressure of step (b) is lower than that of a control genetically modified mouse which does not receive the administration of the drug candidate.

According to some embodiments of the present disclosure, the method of identifying a drug for treating hypertension in a subject by using the genetically modified mouse of the present disclosure may alternatively comprises, (a) measuring the blood pressure of the genetically modified mouse;

(b) administering a drug candidate to the genetically modified mouse;

(c) measuring the blood pressure of the genetically modified mouse of step (b); and (d) identifying the drug candidate to be the drug when the measured blood pressure of step (c) is lower than that of the measured blood pressure of step (a).

According to various embodiments of the present disclosure, the drug candidate is amlodipine, hydralazine, captopril, or valsartan.

The subject is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings briefly discussed below.

FIG. 1 depict the expression percentage (%) of mouse anion exchanger-1 (AE1; band 3) in the erythrocyte membrane (ghost) of GYP.Mur knock-in (GPMur KI) mice or wild-type (control) mice according to Example 2 of the present disclosure. Each dot represents the measurement of a mouse. The data was presented as mean±SD. **$P<0.01$ deemed significant by unpaired t-test.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "genetically modified" refers to a subject (e.g., an animal, cell, or organism) in which a genomic DNA sequence has been deliberately modified by recombinant technology. The term "genetically modified" as used herein encompasses the term "transgenic". The term "genetically modified mouse" refers to a mouse having a genetic modification (e.g., an insertion of an exogenous DNA) in at least one chromosome of the its genome. In some embodiments, at least one or more cells, e.g., at least 1%, 2%, 3%, 4%, 5%, 10%, 20%, 30%, 40%, 50%, 60%, 70%, 80% or 90%, or 100% of cells of the genetically-modified mouse have the genetic modification in its genome. The animals are generally able to pass the modification to progeny, i.e., through germline transmission.

The term "transgene" refers to a nucleotide sequence which is partly or entirely heterologous (i.e., foreign) to the transgenic animal (e.g., transgenic mouse) into which it is introduced. As used herein, the transgene may be operably linked to an endogenous promoter that drives the expression of the transgene in the transgenic mouse, and optionally one or more regulatory sequences necessary for optimal expression of the transgene.

The term "complementary deoxyribonucleic acid" (cDNA) refers to a DNA molecule that may be prepared by reverse transcription from a mature, spliced, messenger ribonucleic acid (mRNA) molecule obtained from a eukaryotic cell (e.g., human cell). As known to a person having an ordinary skill in the art, the cDNA lacks intron sequences that are usually present in the corresponding genomic DNA. The initial, primary RNA transcript is a precursor to mRNA that is processed through a series of steps (e.g., removing the intron sequences via RNA splicing) before appearing as mature spliced mRNA. Thus, the cDNA derived from mRNA lacks any intron sequences.

As discussed herein, minor variations in the amino acid sequences of polypeptides or in the nucleotide sequences of nucleic acids are contemplated as being encompassed by the presently disclosed and claimed inventive concept(s), providing that the variations in the amino acid sequence/nucleotide sequence maintain at least 85% sequence identity, such as at least 85%, 86%, 87%, 88%, 89%, 90%, 91%, 92%, 93%, 94%, 95%, 96%, 97%, 98% and 99% sequence identity. Polypeptides or polynucleotides of the present disclosure may be modified specifically to alter a feature of the polypeptide or polynucleotide unrelated to its physiological activity. For example, certain amino acids can be changed and/or deleted without affecting the physiological activity of the polypeptide in this study. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site.

"Percentage (%) sequence identity" is defined as the percentage of amino acid residues/nucleotides in a candidate sequence that are identical with the amino acid residues/nucleotides in the specific amino acid sequence/nucleotide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences/nucleotide sequences was carried out by computer program Blastp (protein-protein BLAST)/Blastn (nucleotide-nucleotide BLAST) provided online by Nation Center for Biotechnology Information (NCBI). The percentage amino acid sequence/nucleotide sequence identity of a given amino acid sequence/nucleotide sequence A to a given amino acid sequence/nucleotide sequence B (which can alternatively be phrased as a given amino acid sequence/nucleotide sequence A that has a certain % amino acid sequence/nucleotide sequence identity to a given amino acid sequence/nucleotide sequence B) is calculated by the formula as follows:

$$\frac{X}{Y} \times 100$$

where X is the number of amino acid residues/nucleotides scored as identical matches by the sequence alignment program BLAST in that program's alignment of A and B, and where Y is the total number of amino acid residues/nucleotides in A or B, whichever is shorter.

As used herein, the terms "link," "couple," and "conjugate" are used interchangeably to refer to any means of connecting two components either via direct linkage or via indirect linkage between two components.

The term "administered", "administering" or "administration" are used interchangeably herein to refer a mode of delivery, including, without limitation, orally, intravenously, intraperitoneally, intraarterially, or subcutaneously administering an agent (e.g., a test drug) of the present invention.

II. Description of the Invention

GP.Mur, previously known as "Mi.III" is one of several antigens of the MNS blood group system; it is a glycophorin B-A-B hybrid protein evolved from homologous gene recombination between glycophorin B (GYPB) and glycophorin A (GYPA) genes. The GYPA gene is present in both human and mouse genomes, while GYPB and GYPB-derived GYP.Mur genes are only present in human genome. It is known that the human subjects having the GP.Mur type (GP.Mur$^+$ subject) have slightly higher blood pressure (BP) as compared to the human subjects lacking the GP.Mur type (GP.Mur$^-$ subject). Accordingly, the transgenic animal expressing the GP.Mur protein may serve as an animal model for selecting or identifying anti-hypertension drugs. The present disclosure thus provides a genetically modified mouse that functionally expresses the GP.Mur protein, and uses of the genetically modified mouse in selecting or identifying a drug for treating hypertension in a subject, for example, a GP.Mur$^+$ subject.

The first aspect of the present disclosure is directed to a method of producing a genetically modified mouse whose genome comprises a transgene encoding GP.Mur (Mi.III antigen). The method comprises, (a) introducing the transgene into the genome of a mouse zygote or embryo; and (b) transplanting the mouse zygote or embryo of step (a) into a recipient mouse to produce the genetically modified mouse.

In step (a), the transgene encoding GP.Mur is introduced into the GYPA gene of a zygote or embryo of *Mus musculus*. According to some embodiments of the present disclosure, the transgene is introduced into the GYPA gene of C57BL/6J mouse. The mouse GYPA gene (Gene ID: 14934) comprises 8 exons, and the mRNA transcribed therefrom comprises 1827 nucleotides in its length (NCBI Reference Sequence: NM_010369.3), as reported by M Terajima et al. in "Structural organization of the mouse glycophorin A gene" (*J. Biochem* 116 (5): 1105-10 (1994)). The publication is incorporated herein by reference in its entirety. In the embodiments of the present disclosure, the transgene is introduced into the 3' UTR of the GYPA gene of the zygote or embryo.

According to some embodiments of the present disclosure, the step (a) is carried out by use of clustered, regularly interspaced short palindromic repeats (CRISPR)/CRISPR-associated protein 9 (Cas9) system, a technology widely used in the art to selectively modify the DNA (e.g., editing the genome) of living organisms. In general, the CRISPR/Cas9 system is composed of a noncoding single guide sequence (sgRNA) and a Cas9 nuclease. The sgRNA consists of two components, which are a target-specific fragment (i.e., CRISPR RNA (crRNA)) and a scaffold fragment linked to the terminus (e.g., 3' end) of the target-specific fragment, in which the scaffold fragment comprises an auxiliary trans-activating crRNA (tracrRNA) and optionally a linker linking the tracrRNA to the crRNA. The sgRNA guides the Cas9 protein to a specific genomic locus, where the Cas9 nuclease induces a double-stranded break (DSB) at the specific genomic target sequence. The DSB can be repaired by non-homologous end joining (NHEJ) process or homology-directed repair (HDR) process. Specifically, in the absence of a repair template, the NHEJ process usually results in gene insertions or deletions (indels) around the DSB. Alternatively, in the case when a repair template (i.e., a donor template) is present, then a designed sequence may be introduced at a specific locus within the genome via the HDR process.

According to some embodiments of the present disclosure, the transgene is introduced into the GYPA gene by the CRISPR/Cas9 system with the aid of a donor template comprising the transgene. In these embodiments, the sgRNA targeting the 3' UTR of mouse GYPA gene comprises a target-specific fragment (crRNA) having the nucleotide sequence of "5'-TGAGGTCTTTCAAACATTGG-3'" (SEQ ID NO: 4) that allows the Cas9 protein to recognize and produce a DSB at the 3' UTR of GYPA gene. As described above, in addition to the target-specific fragment (crRNA), the sgRNA preferably further comprises a scaffold fragment facilitating the processing and function of the target-specific fragment. According to one exemplary embodiment of the present disclosure, the scaffold fragment comprises the amino acid sequence of SEQ ID NO: 9; in this case, the sgRNA comprises the amino acid sequence of SEQ ID NO: 5.

Regarding the donor template, it comprises a 5' homologous arm (5' HR), the transgene, and a 3' homologous arm (3' HR), from 5' end to 3' end, in sequence. According to the embodiments of the present disclosure, the 5' and 3' HRs respectively comprise the nucleotide sequences homologous to the sequences upstream and downstream of the DSB produced by the sgRNA. In this way, the transgene flanked by the 5' and 3' HRs may be introduced into the 3' UTR of GYPA gene via homologous recombination between the homologous arms and the 3' UTR sequence. According to one embodiment, the 5' HR comprises the nucleotide sequence of SEQ ID NO: 7, and the 3' HR comprises the nucleotide sequence of SEQ ID NO: 8.

Depending on desired purpose, the donor template may be a plasmid or single strand DNA (ssDNA). According to one exemplary embodiment of the present disclosure, the donor template is a plasmid that release the transgene via endonuclease (e.g., nicking endonuclease Nb.BbvCI).

According to some embodiments of the present disclosure, the transgene is the cDNA of GYP.Mur gene (GYP.Mur cDNA) that comprises the nucleotide sequence of SEQ ID NO: 2, and encodes the GP.Mur (Mi.III) protein comprising the amino acid sequence of SEQ ID NO: 1. As could be appreciated, the present GYP.Mur cDNA may be modified to comprise one or more degenerate nucleotides as long as the protein (i.e., the GP.Mur protein) encoded by the degenerate nucleotide sequence maintains the desired activity or function. The term "degenerate nucleotide sequence" (also known as "nucleotide degeneracy") denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp). Accordingly, the nucleotide sequences comprising degenerate nucleotide(s) are intended to be included within the scope of the present disclosure, providing that the variations in the nucleotide sequence maintain at least 85% sequence identity to SEQ ID NO: 2, such as at least 85%, 86%, 87%, 88%, 89%, 90%, 91%, 92%, 93%, 94%, 95%, 96%, 97%, 98% or 99% sequence identity to SEQ ID NO: 2.

According to some embodiments of the present disclosure, in addition to GYP.Mur cDNA, the transgene further comprises a bicistronic element linked to the 5' end of GYP.Mur cDNA. Depending on intended purpose, the bicistronic element may be an IRES, a 2A peptide, or any sequences or peptides known to express multiple proteins from one transcript. IRES is a sequence that recruits ribosomes and allows cap-independent translation. In practice, IRES serves as a linker linking two coding sequences in one bicistronic sequence and allowing the translation of both proteins in cells. The 2A peptide also known as "2A self-cleaving peptide" is a class of peptide having 18 to 22 amino acid residues in length, which can induce ribosomal skipping during translation of a protein in cells. According to one exemplary embodiment of the present disclosure, the bicistronic element is IRES, and the transgene including IRES and GYP.Mur cDNA comprises the nucleotide sequence of SEQ ID NO: 3. As described above, the nucleic acid may be modified to comprise one or more degenerate nucleotides as long as the protein (i.e., the GP.Mur protein) encoded thereby maintains the desired activity or function. Accordingly, the nucleotide sequences comprising degenerate nucleotide(s) are contemplated in the scope of the present disclosure, providing that the variations in the nucleotide sequence maintain at least 85% sequence identity to SEQ ID NO: 3, such as at least 85%, 86%, 87%, 88%, 89%, 90%, 91%, 92%, 93%, 94%, 95%, 96%, 97%, 98% or 99% sequence identity to SEQ ID NO: 3.

For the purpose of editing the genome of the mouse zygote or embryo, the sgRNA and donor template as described above are mixed with Cas9 protein and microinjected into the mouse zygote or embryo so that the transgene carried by the donor template is introduced into the genome (the 3' UTR of GYPA gene) of the mouse zygote or embryo.

As could be appreciated, the step (a) may alternatively be carried out by other gene knock-in technologies, for example, the Cre/LoxP recombination system, the Flp/FTR recombination system, or the phiC31 integrase system.

In the step (b), the mouse zygote or embryo having the transgene incorporated in its genome is transplanted into the uterine tube (also known as "fallopian tube" or "oviduct") or uterus of the recipient female mouse to produce the genetically modified mouse. The thus-produced genetically modified mouse comprises GYP.Mur cDNA in its genome (at 3' UTR of GYPA gene) and expresses the GP.Mur (Mi.III) protein.

The second aspect of the present disclosure thus pertains to a genetically modified mouse (hereinafter as "GYP.Mur knock-in mouse") that comprises GYP.Mur cDNA in its genome and expresses the GP.Mur (Mi.III) protein. According to the embodiments of the present disclosure, the GP.Mur protein comprises the amino acid sequence of SEQ ID NO: 1.

As described above, GYP.Mur cDNA is at the 3' UTR of GYPA gene of the GYP.Mur knock-in mouse, and comprises a nucleotide sequence at least 85% identical to SEQ ID NO: 2. In one specific example, GYP.Mur cDNA comprises a nucleotide sequence 100% identical to SEQ ID NO: 2.

According to certain embodiments of the present disclosure, the GYP.Mur knock-in mouse has the GP.Mur protein expressed on the erythrocyte membrane thereof According to some embodiments of the present disclosure, compared to wild-type mouse, the GYP.Mur knock-in mouse has higher blood pressure.

Also disclosed herein is a method of identifying a drug for treating hypertension by using the GYP.Mur knock-in mouse of the present disclosure. The method comprises, (i) administering a drug candidate to the GYP.Mur knock-in mouse;

(ii) measuring the blood pressure of the genetically modi-
fied mouse of step (i); and (iii) identifying the drug candidate to be the drug when the
measured blood pressure of step (ii) is lower than that
of a control genetically modified mouse, which does
not receive the administration of the drug candidate.

In step (i), the drug candidate is administered to the
GYP.Mur knock-in mouse via a suitable route, for example,
oral, intravenous, intraperitoneal, intraarterial, or subcuta-
neous injection. According to some embodiments of the
present disclosure, the drug candidate is orally administered
to the GYP.Mur knock-in mouse.

In step (ii), the blood pressure of the GYP.Mur knock-in
mouse receiving administration of the drug candidate is
measured. The measurement may be carried out by using
any devices or systems known to monitor or determine the
blood pressure of mice, for example, the CODA® high
throughput monitoring system.

In step (iii), the drug for treating hypertension is identified
based on the result of step (ii). Specifically, the blood
pressure measured in step (ii) is compared to the blood
pressure of a control GYP.Mur knock-in mouse (i.e., a
GYP.Mur knock-in mouse which does not receive adminis-
tration of the drug candidate). In the case when the blood
pressure measured in step (ii) is lower than that of the
control GYP.Mur knock-in mouse, then the drug candidate
is identified as the drug useful for treating hypertension. By
contrast, in the case when the blood pressure measured in
step (ii) equals to or is higher than that of the control
GYP.Mur knock-in mouse, then the drug candidate is not a
drug suitable to treat hypertension.

Alternatively, the drug for treating hypertension may be
identified by comparing the blood pressures of a GYP.Mur
knock-in mouse prior to and after administration of a drug
candidate. In the aspect, the present method comprises, (i) measuring the blood pressure of the GYP.Mur knock-
in mouse;

(ii) administering the drug candidate to the GYP.Mur
knock-in mouse;

(iii) measuring the blood pressure of the GYP.Mur knock-
in mouse of step (ii); and (iv) identifying the drug candidate to be the drug when the
measured blood pressure of step (iii) is lower than the
measured blood pressure of step (i).

According to certain embodiments of the present disclo-
sure, in the case when the blood pressure measured in step
(iii) is lower than the measured blood pressure of step (i),
then the drug candidate is identified as the drug useful for
treating hypertension. By contrast, in the case when the
blood pressure measured in step (iii) equals to or is higher
than the measured blood pressure of step (i), then the drug
candidate is not a drug suitable to treat hypertension.

According to various embodiments of the present disclo-
sure, the drug candidate is amlodipine, hydralazine, capto-
pril, or valsartan.

The subject is a mammal; preferably, a human. According
to some embodiments of the present disclosure, the subject
is a human, who has Mi.III antigen expressed on the
erythrocyte membrane thereof, i.e., having the GP.Mur
blood type (GP.Mur$^+$ subject). According to alternative
embodiments of the present disclosure, the subject is a
human, who does not express GP.Mur type, i.e., GP.Mur$^-$
subject.

The following Examples are provided to elucidate certain
aspects of the present invention and to aid those of skilled in
the art in practicing this invention. These Examples are in no
way to be considered to limit the scope of the invention in any manner. Without further elaboration, it is believed that
one skilled in the art can, based on the description herein,
utilize the present invention to its fullest extent. All publi-
cations cited herein are hereby incorporated by reference in
their entirety.

EXAMPLE

Materials and Methods

Generation of Human GYP.Mur Knock-In Mice

GYP.Mur knock-in mice (C57BL/6JNarl-Gypa$^{em1}$
$_{(GYPMur)MMH}$) was generated by CRISPR/Cas9-mediated
DNA cleavage and homologous recombination with a
replacing ssDNA on mouse GYPA allele. The recombinant
*Streptococcus pyogenes* Cas9 protein containing multiple
nuclear localization sequences (NLSs). The single guide
RNAs (sgRNA) consisted of a 20-nt guide sequence (SEQ
ID NO: 4) and an 80-mer "Synthego scaffold" (SEQ ID NO:
9). The replacing single strand DNA (ssDNA) were released
from the targeting vector pUC57-GypaHR-IRES-GYP-Mur,
which comprised a 5' HR, an IRES, a human GYP.Mur
cDNA and a 3' HR (from 5' end to 3' end, in sequence), by
digestion with nicking endonuclease Nb.BbvCI and dena-
turation with formamide. GYP.Mur cDNA comprised a
nucleotide sequence of SEQ ID NO: 2. Mouse zygotes were
obtained by mating superovulated C57BL/6 females and
males. The sgRNA, Cas9 protein, and replacing ssDNA
were mixed just before microinjection into the pro-nuclei of
the zygotes. The microinjected embryos were incubated at
37° C. before being transplanted to pseudopregnant females
on the same day.

To determine whether knock-in of GYP.Mur was success-
ful, mouse genomic DNA was extracted from tail tips of the
pups and then subjected to PCR-sequencing using the fol-
lowing primer sets: 5F (5'-GGCAT-
CAATCGGCAAGAATG-3'; SEQ ID NO: 10), 5B (5'-
GTCGCTTTCAACCACGCAAG-3'; SEQ ID NO: 11), 3F
(5'-GTGATGGCTGGTATTATTGGAACG-3'; SEQ ID NO:
12), and 3B (5'-AATGAGGGCTGTGAGTGTCCTTAC-3';
SEQ ID NO: 13). The expected sizes of the PCR products
using the primer sets 5F+5B and 3F+3B were 828 and 730
bp, respectively.

Housing and Breeding of GYP.Mur Knock-In Mice

All mice were ear tagged and housed separately by sex.
Unless specified, they were housed in 47.5 cm×25.8
cm×21.2 cm cages, each with a completely covered top filter
and wood shaving bedding under a 12:12 dark/light cycle, at
constant temperature between 20-25° C. and relative humid-
ity between 50-70%. Their water and food were supplied ab
libitum. For two or more weeks of mating, mice were
weighted before being transferred in pairs (1 male and 1
female per pair) to small cages (29.6 cm×18.8 cm×13.6 cm)
covered with nesting materials (i.e., tissue strips). After
giving birth, pups were weaned between the 21$^{st}$ and the 28$^{th}$
days; their genomic DNA was extracted from individual tail
tissues during this period. PCR-sequencing was used to test
whether the pups carried GYP.Mur gene.

For the first three generations following the GYP.Mur
knock-in founder (F$_0$), hemizygous GYP.Mur knock-in mice
were crossed with wild-type C57BL/6J (B6J) mice to mini-
mize CRISPR/Cas 9-related off-target effects/mosaicism
and to increase the chances of successful reproduction. The
GYP.Mur knock-in mice were intercrossed from the 4$^{th}$
generation. The data presented here were from homozygous
male GYP.Mur knock-in mice from the 5$^{th}$ to the 9$^{th}$ gen-
erations.

Reverse Transcription-Polymerase Chain Reaction (RT-PCR) for GYP.Mur Transcript in Peripheral Blood Peripheral blood samples were collected from 6 mice per group. The pooled whole blood samples in acid citrate dextrose (ACD) tubes from 6 mice were subjected to total RNA extraction, reverse transcription, and then PCR. The forward and reverse primers for amplifying the GYP.Mur cDNA by PCR comprised the nucleotide sequences of "5'-CAGACAAATGATAAGCAC-3'" (SEQ ID NO: 14; comprising the ending sequence of exon 2 and the beginning sequence of exon 3) and "5'-GGCAT-AAGCAAAGGAATAGCAGG-3'" (SEQ ID NO: 15), respectively. The forward and reverse primers for amplifying the GAPDH cDNA by PCR comprised the nucleotide sequences of "5'-GTTGTCTCCTGCGACTTCA-3'" (SEQ ID NO: 16) and "5'-GGAAGATGGTGATGGGATT-3'" (SEQ ID NO: 17), respectively.

Determination of the Expression of Mouse AE1 Protein by Enzyme-Linked Immunosorbent Assay (ELISA)

When mice were over 6 weeks old and with body weights over 20 g each, 50-100 μL blood was withdrawn for protein analyses. The membrane fraction (ghost) of red blood cell (RBC) was isolated by hypotonic rupture and then centrifugal fractionation at 2-4° C. The RBC membrane fraction of each mouse was solubilized in an equal volume of the doubly-concentrated, ice-cold lysis buffer (the final composition of the buffer after mixing with an equal volume of the 2× lysis buffer: 1% NP-40 in phosphate buffered saline (PBS) supplemented with protease inhibitor cocktails). The mixture was subjected to the freeze-and-thaw treatment for three times at 2-4° C. to disrupt the membrane structure. Protein concentrations of the lysates were determined by the Lowry method.

In the AE1 sandwich ELISA, an ELISA plate was coated with a mouse monoclonal antibody (mAb) targeting the C-terminal, cytoplasmic sequence of human and mouse AE1, and incubated at 4° C. overnight. Each mouse lysate sample (2 μg) was individually added to a well and incubated for 2 hours at 37° C., followed by PBS washes. A rabbit polyclonal antibody (mBRIC 6; 1:50,000 to 1:100,000 dilution) against the extracellular sequence of mouse AE1 serving as a AE1-detecting antibody was added to the well. The plate was incubated for 1.5 hours at 37° C. and then subjected to PBS washes. A horseradish peroxidase (HRP)-conjugated anti-rabbit secondary antibody (1:3,000 dilution) was added to each well, and incubated at 37° C. for 30 minutes for signal amplification and AE1 expression quantitation.

For calibration in this ELISA, the peptide used to immunize the rabbits to produce the mBRIC 6 antibody (AA 564-585: QDYPLQQTYAPVVMKPKPQGPV; SEQ ID NO: 18) was serially diluted and then coated onto the same ELISA plate overnight at 4° C. The wells coated with different concentrations of the mBRIC 6 peptide were incubated with mBRIC 6 antibody and then with HRP-conjugated anti-rabbit secondary antibody, at the same time as the lysate samples were added.

Complete Blood Count (CBC) and Serum Biochemical Tests

For CBC, about 100 μL of whole blood was collected from the facial vein of a mouse using a lancet. CBC was performed on the whole blood samples collected in ethylenediaminetetraacetic acid (EDTA)-containing microtubes by a hematology analyzer.

To evaluate renal functions and serum lipids, at least 100 μL of blood per mouse was collected into a serum separation tube, followed by 10 minutes of 1500×g centrifugation. Serum creatinine (CRE), urea nitrogen (BUN), uric acid (UA), triglyceride (TG), and total cholesterol (T-CHO) were analyzed using an automatic clinical chemistry analyzer.

Measurement of Murine Blood Pressure (BP)

Mouse BP was measured using an 8-channel non-invasive blood pressure system, a conventional instrument for murine BP measurements with about 99% correlation to the invasive telemetry approach. The BP system is a traditional, tail-cuff method, with a volume-pressure recording (VPR) sensor-cuff (similar to a stethoscope) and an occlusion cuff (similar to the arm cuff for conventional human BP measurement). The instrument settings in this study were 5 acclimation cycles, 15 cycles per set, 250 mmHg as the maximal occlusion pressure, and 20 seconds for deflation. Before the measurement, the experimenter gently placed a mouse in a holder or at the entry point of the holder, from which the mouse could voluntarily walked into the holder. An occlusion cuff and a VPR cuff were then fitted onto the mouse tail. The holder carrying a cuffed mouse inside was moved to the warming platform and covered with a thermal blanket, which ensured the temperature of the tail to be within 32-35° C. during volume-pressure-based BP measurements. Invalid measurements were mostly due to unmet tail temperature or restless states of the animal, which were identified and excluded. After BP measurements, the mice were immediately put back to their own cage.

Evaluation of Anti-Hypertensive Medications

The body weight (BW) of each mouse was measured for preparation of individual anti-hypertensive doses (in mg drug per Kg BW). The mice were individually administered by oral gavage of an anti-hypertensive drug mixed in 100 μL autoclaved ddH₂O. The dose and maximal efficacy of an anti-hypertensive drug was determined based on the degrees of BP drop within an hour of anti-hypertensive administration.

One dose of an anti-hypertensive drug was tested on a single day. On the morning of the test day, the blood pressure of GYP.Mur knock-in mice and age-matched control mice (wild-type mice) was first measured. Only the mice with SBP>120 mmHg on that day were tested with an anti-hypertensive medication. The BP and heart rates (HR) of the mice were measured at the $1^{st}$, $3^{rd}$, $5^{th}$, and the $24^{th}$ hour post-medication. The BP data collected 24 hours later were used to ensure that the BP-lowering effects of the drug have been cleared. The tested animals were given at least 1-3 days of rest before the next anti-hypertensive drug test.

Example 1 Characterization of GYP.Mur Knock-In Mice

As described in Materials and Methods, the humanized GYP.Mur transgene mice were created by inserting human GYP.Mur cDNA into the 3' untranslated region (UTR) of murine GYPA gene using CRISPR/Cas 9-mediated homologous recombination. To reduce deleterious off-target effects and mosaicism from CRISPR/Cas 9-induced gene recombination, GYP.Mur knock-in founders (F₀) were crossed with wild-type B6J mice for three generations. The hemizygotic GYP.Mur knock-in mice were then intercrossed to obtain the first homozygous GYP.Mur knock-in mice, and produced stable homozygous progenies by intercrossing homozygous GYP.Mur knock-in mice from the $5^{th}$ to the $9^{th}$ generations (all the data presented here were from male mice of these five generations, as female mice spent most time in pregnancy or nurturing the pups). Homozygous GYP.Mur knock-in pups had 100% postnatal survival and a roughly 1:1 sex ratio which follows the Mendelian prediction. Knock-in of GYP.Mur did not affect general health or longevity of C57BL/6J mice.

According to the RT-PCR analysis, the GYP.Mur transcript was only present in the peripheral blood of GYP.Mur knock-in mice, and absent in the control mice (data not shown).

Example 2 Increased AE1 Expression on the RBC Membrane of GYP.Mur Knock-In Mice As demonstrated in human RBCs and heterologously expressed cultured cells (e.g., transfected HEK-293 cells), GP.Mur enhanced AE1 expression via assisting AE1 protein folding and stabilizing AE1 complexes on the cell membrane. Accordingly, the mouse AE1 expression on the RBCs from GYP.Mur knock-in mice and wild-type control mice were determined by mouse AE1-specific sandwich ELISA.

wild-type B6J mice (averaged MCHC was about 30.2 g/L with 95% CI ranging between 24.6 g/L to 34.9 g/L]). Importantly, the GYP.Mur knock-in male mice from these five generations (3-11 months old) exhibited 8-26 mmHg higher systolic blood pressure (SBP) and 6-27 mmHg higher diastolic blood pressure (DBP), as compared to age-matched control male mice (Table 1). Their differences in mean arterial pressure (MAP) were 15-27 mmHg at the ages between 3 and 9 months old (equivalent to mature/middle-aged human), and then reduced to 7-8 mmHg at 11 months old (roughly corresponding to human age of 54 years). Notably, the blood pressure of both GYP.Mur knock-in mice and control B6J mice decreased significantly after 9 months old (about human age of 46 years); their BP differences diminished when the two groups of mice were over one year old (Table 1).

TABLE 1

| Cardiovascular parameters of GYP.Mur KI versus the control mice at different ages | | | | | | |
|---|---|---|---|---|---|---|
| Cardiovascular | 3-month-old | | | 5-month-old | | |
| parameter | control (9) | GYP.Mur KI (6) | p-value | control (9) | GYP.Mur KI (7) | p-value |
| SBP (mmHg) | 141.8 ± 11.1 | 164.6 ± 13.1 | p* < 0.05 | 127.4 ± 13.5 | 143.0 ± 11.0 | p* < 0.05 |
| DBP (mmHg) | 109.5 ± 10.9 | 134.5 ± 12.8 | p* < 0.05 | 93.9 ± 11.7 | 108.4 ± 10.2 | p* < 0.05 |
| MAP (mmHg) | 119.9 ± 10.9 | 144.2 ± 12.9 | p* < 0.05 | 104.7 ± 12.3 | 119.6 ± 10.4 | p* < 0.05 |
| PP (mmHg) | 32.2 ± 3.6 | 30.1 ± 1.8 | n.s. | 33.4 ± 2.1 | 34.6 ± 1.7 | n.s. |
| Heart rate (/min) | 521.5 ± 103.2 | 582.0 ± 42.9 | n.s. | 480.3 ± 52.7 | 494.4 ± 53.4 | n.s. |
| Cardiovascular | 9-month-old | | | 11-month-old | | |
| parameter | control (8) | GYP.Mur KI (9) | p-value | control (16) | GYP.Mur KI (10) | p-value |
| SBP (mmHg) | 102.7 ± 16.1 | 128.5 ± 16.0 | p* < 0.05 | 99.0 ± 7.0 | 107.4 ± 10.8 | p* < 0.05 |
| DBP (mmHg) | 73.3 ± 12.3 | 100.7 ± 16.6 | p* < 0.05 | 71.6 ± 5.6 | 78.0 ± 8.8 | p* < 0.05 |
| MAP (mmHg) | 82.8 ± 13.6 | 109.6 ± 16.3 | p* < 0.05 | 80.2 ± 5.8 | 87.6 ± 9.5 | p* < 0.05 |
| PP (mmHg) | 29.3 ± 5.0 | 27.8 ± 2.9 | n.s. | 27.4 ± 3.5 | 29.4 ± 3.4 | n.s. |
| Heart rate (/min) | 517.5 ± 90.9 | 553.8 ± 63.7 | n.s. | 466.6 ± 84.4 | 503.7 ± 76.4 | n.s. |

1. SBP: systolic blood pressure; DBP: diastolic blood pressure; MAP: mean arterial pressure; PP: pulse pressure.
2. n.s.: no significance.
3. The number in bracket indicates the number of animals.

The data indicated that the AE1 expression level on the RBCs of GYP.Mur knock-in mice were significantly higher than that in control mice (FIG. 1). According to the results, knock-in of human GYP.Mur resulted in about 55% increase of murine AE1, in which AE1 represented $2.7 \pm 0.7\%$ of all membrane proteins (w/w) on the RBCs of the control mice, and $4.2 \pm 1.2\%$ of all membrane proteins on the RBCs of GYP.Mur knock-in mice (FIG. 1; **p<0.01).

Example 3 Higher Blood Pressure in GYP.Mur Knock-In Mice

It is known that healthy people bearing the GP.Mur blood type exhibit slightly lower hemoglobin (Hb) and mean corpuscular hemoglobin concentration (MCHC), and slightly higher blood pressure (all within the normal ranges); and their Hb-BP correlation appears stronger than people lacking the phenotype. The CBC data of GYP.Mur knock-in mice were also within the normal range of wild-type B6J mice (data not shown). Notably, MCHC values from different generations of GYP.Mur knock-in mice were all slightly lower than the MCHC values of age-matched control mice, with statistical significance (GYP.Mur knock-in mice: $28.5 \pm 0.3$ g/dL, control mice: $29.2 \pm 0.5$ g/dL). The slightly lower MCHC values were still within the normal range for The apparent 7.4-26.8 mmHg higher MAP in GYP.Mur knock-in mice than age-matched control mice at 3-11 months old indicating that GP.Mur/increased AE1 expression could trigger hypertension directly. To identify potential factors contributing to GP.Mur-induced hypertension, the body weights, kidney functions and lipid profiles of the GYP.Mur knock-in mice and wild-type control mice. The data indicated that there were no abnormalities or significant differences between the two groups of mice (data not shown). Serum creatinine was similar between GYP.Mur knock-in mice and age-matched control mice, and all were within the normal range (mean creatinine was 0.3 mg/dL with 95% CI ranging from 0.2 mg/dL to 0.5 mg/dL). The blood urea nitrogen (BUN) of the mice was also comparable and within the normal range, indicating undisturbed renal function by GP.Mur expression. The GYP.Mur knock-in mice even exhibited slightly lower serum uric acid than age-matched control mice (*p<0.05; data not shown). On the other hand, the averaged level of total cholesterol (TCHO) in GYP.Mur knock-in mice was about 19 mg/dL higher than that of the control mice (data not shown), though their cholesterol, triglyceride (Tg) and body weights were all within the normal ranges of B6J mice (mean Tg was 157 mg/dL with 95% CI ranging from 67 mg/dL to 278 mg/dL, and mean TCHO was 114 mg/dL with 95% CI ranging from 69 mg/dL to 169 mg/dL). Thus, GP.Mur-triggered hypertension was unlikely due to metabolic, lipid or kidney function abnormalities (data not shown).

Despite of bearing ≥20 mmHg higher BP, the middle-aged GYP.Mur knock-in mice could run as well as age-matched control mice on a rodent treadmill for over one hour before reaching exhaustion (maximal endurance running distance before exhaustive stop, in which the running distance of 5-month-old GYP.Mur knock-in mice and 5-month-old control mice were respectively 1134.7±232.2 m and 1073.3±167.7 m; no significant differences). The levels of the serum NT proBNP (a cardiovascular disease marker elevated by ventricular pressure overload and myocardial overstretch) between GYP.Mur knock-in mice and control mice were also similar and unremarkable. Since these two groups of mice were on normal chow and were not stressed (e.g., metabolic insult by high-fat diet), GP.Mur-associated hypertension may be considered "preclinical grade" and not yield cardiovascular complications in the absence of a stressor.

Example 4 Differential Antihypertensive Drug Sensitivities

The GYP.Mur knock-in mice were tested with different categories of anti-hypertensive drugs. The GYP.Mur knock-in mice and control mice between 4-6 months old and with SBP>120 mmHg in the morning of the test day were selected for anti-hypertensive treatments (the latter requirement was to prevent accidental death due to extreme hypotension caused by the medication). As C57BL/6J is not a hypertensive strain, significantly fewer wild-type B6J mice were qualified to be put in the anti-hypertensive drug tests (data not shown).

Three anti-hypertensive drugs were tested, including amlodipine (a dihydropyridine calcium channel blocker (CCB)), hydralazine (a direct arterial vasodilator), and captopril (a angiotensin converting enzyme (ACE) inhibitor). All of the drugs effectively lowered BP in both control and GYP.Mur knock-in mice, but with distinct features. As a long-acting anti-hypertensive for human, amlodipine also sustained BP-lowering effects in these mice for 5 hours following oral gavage. In contrast, both captopril and hydralazine lowered BP most substantially one hour after medication, and then their BP-lowering effects slightly diminished at the $3^{rd}$ hour post-oral gavage (data not shown).

Both amlodipine and hydralazine were significantly more effective in lowering BP in GYP.Mur knock-in mice than in control mice; in contrast, captopril exhibited similar efficacy in lowing BP of both control and GYP.Mur knock-in mice (data not shown). As the pharmacological mechanisms of these anti-hypertensive drugs are intricately related, the GYP.Mur knock-in model is useful in delineating anti-hypertensive mechanisms and developing therapeutic strategies.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A genetically modified mouse whose genome comprises a transgene encoding a Miltenberger blood group antigen subtype III (Mi.III antigen) comprising the amino acid sequence of SEQ ID NO: 1, wherein the transgene comprises a nucleotide sequence at least 85% identical to SEQ ID NO: 3.

2. The genetically modified mouse of claim 1, wherein the transgene is a complementary deoxyribonucleic acid (cDNA) of GYP.Mur gene and comprises a nucleotide sequence at least 85% identical to SEQ ID NO: 2.

3. The genetically modified mouse of claim 2, wherein the transgene comprises a nucleotide sequence 100% identical to SEQ ID NO: 2.

4. The genetically modified mouse of claim 1, wherein the transgene comprises an internal ribosome entry site (IRES), and a cDNA of GYP.Mur gene that is linked to the 3' end of the IRES.

5. The genetically modified mouse of claim 1, wherein the transgene comprises a nucleotide sequence 100% identical to SEQ ID NO: 3.

6. The genetically modified mouse of claim 1, wherein the transgene is at the 3' untranslated region (UTR) of an endogenous glycophorin A (GYPA) gene of the genetically modified mouse.

7. A method of producing the genetically modified mouse of claim 1 comprising, (a) introducing the transgene into an endogenous GYPA gene of a zygote or embryo of a mouse by (a-1) providing a single guide ribonucleic acid (sgRNA) comprising the nucleotide sequence of SEQ ID NO: 4;

(a-2) providing a donor template comprising the transgene, a 5' homologous arm, and a 3' homologous arm, wherein the 5' and 3' homologous arms are respectively linked to the 5' end and 3' end of the transgene, and respectively comprise the nucleotide sequences of SEQ ID NOs: 7 and 8;

(a-3) injecting the sgRNA of (a-1), the donor template of (a-2) and a CRISPR associated protein 9 (Cas9) into the zygote or embryo; and (b) transplanting the zygote or embryo of (a) into a recipient mouse to produce the genetically modified mouse.

8. The method of claim 7, wherein the transgene is a cDNA of GYP.Mur gene and comprises a nucleotide sequence at least 85% identical to SEQ ID NO: 2.

9. The method of claim 8, wherein the transgene comprises a nucleotide sequence 100% identical to SEQ ID NO: 2.

10. The method of claim 7, wherein the transgene comprises an IRES, and a cDNA of GYP.Mur gene linked to the 3' end of the IRES.

11. The method of claim 10, wherein the transgene comprises a nucleotide sequence at least 85% identical to SEQ ID NO: 3.

12. The method of claim 11, wherein the transgene comprises a nucleotide sequence 100% identical to SEQ ID NO: 3.

13. The method of claim 12, wherein the donor template comprises a nucleotide sequence 100% identical to SEQ ID NO: 6.

14. The method of claim 7, wherein the single guide ribonucleic acid (sgRNA) comprises a nucleotide sequence 100% identical to SEQ ID NO: 5.

15. The method of claim 7, wherein the transgene is introduced into the 3' UTR of the endogenous GYPA gene of the zygote or embryo.

16. A method of identifying a drug for treating hypertension in a subject by using the genetically modified mouse of claim 1, comprising, (a) administering a drug candidate to the genetically modified mouse;

(b) measuring the blood pressure of the genetically modified mouse of (a); and (c) identifying the drug candidate to be the drug when the measured blood pressure of (b) is lower than that of a control genetically modified mouse, which does not receive the administration of the drug candidate;

wherein, the drug candidate is amlodipine, hydralazine, captopril, or valsartan.

17. The method of claim 16, wherein the subject has the Mi.III antigen expressed on an erythrocyte membrane thereof.

\*     \*     \*     \*     \*